(12) United States Patent
Voslar et al.

(10) Patent No.: US 8,143,417 B2
(45) Date of Patent: Mar. 27, 2012

(54) METHOD FOR THE PREPARATION OF ZOLMITRIPTAN

(75) Inventors: Michal Voslar, Praha (CZ); Monika Zatopkova, Ostrava (CZ); Ludek Ridvan, Praha (CZ); Tomas Pekarek, Praha (CZ)

(73) Assignee: Zentiva k.s., Praha (CZ)

( * ) Notice: Subject to any disclaimer, the term of this patent is extended or adjusted under 35 U.S.C. 154(b) by 180 days.

(21) Appl. No.: 12/526,958

(22) PCT Filed: Feb. 25, 2008

(86) PCT No.: PCT/CZ2008/000021
§ 371 (c)(1),
(2), (4) Date: Dec. 17, 2009

(87) PCT Pub. No.: WO2008/104134
PCT Pub. Date: Sep. 4, 2008

(65) Prior Publication Data
US 2010/0105919 A1 Apr. 29, 2010

(30) Foreign Application Priority Data
Feb. 26, 2007 (CZ) .................................... 2007-159

(51) Int. Cl.
*C07D 263/04* (2006.01)
(52) U.S. Cl. ....................................................... 548/229
(58) Field of Classification Search .................... 548/229
See application file for complete search history.

(56) References Cited
FOREIGN PATENT DOCUMENTS
| WO | WO 97/06162 | 2/1997 |
| WO | WO 2005/075467 | 8/2005 |
| WO | WO 2006/055964 | 5/2006 |

OTHER PUBLICATIONS

International Search Report of Application No. PCT/CZ2008/000021 mailed on Feb. 4, 2009.
Swamy G. Y. S. K. et al., "The 1:1 inclusion compounds zolmitriptan-phenol", ACTA Crystallographica, Section C., Crystal Structure Communications, Jul. 2007, vol. 63, No. Pt 7, pp. o437-o440, XP002511429, ISSN:0108-2701.

Primary Examiner — Rebecca Anderson
Assistant Examiner — Samantha Shterengarts
(74) Attorney, Agent, or Firm — Pearl Cohen Zedek Latzer, LLP

(57) ABSTRACT

In the preparation of zolmitriptan of formula III the reduction of the diazonium salt to (5)-4-(4-hydrazinobenzyl)-1,3-oxazolidin-2-one of formula IV is performed in a more concentrated mixture and by the effect on an alkali metal disulphite, preferably sodium disulphite. A zolmitriptan toluene solvate, characterized by a toluene content of 9 to 14% by weight according to the gas chromatography determination and by a maximum of the corresponding mass loss at temperatures of about 111° C. in the gravimetric analysis record. A zolmitriptan toluene solvate, showing strong Raman bands at the wave numbers of 1443 and 1354 cm⁻¹, characteristic for the crystal lattice of zolmitriptan with built-in toluene, and further marked bands at 1004 and 786 cm⁻¹, characteristic for toluene.

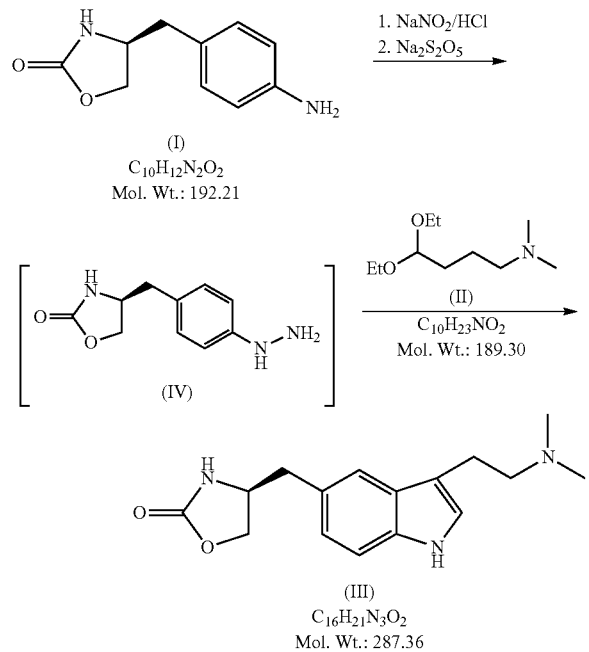

8 Claims, 1 Drawing Sheet

METHOD FOR THE PREPARATION OF ZOLMITRIPTAN

CROSS-REFERENCE TO RELATED APPLICATIONS

This application is a National Phase Application of PCT International Application No. PCT/CZ2008/000021, International Filing Date Feb. 25, 2008, claiming priority of Czech Republic Patent Application, PV 2007-159, filed Feb. 26, 2007.

TECHNICAL FIELD

The invention deals with a method of manufacturing (S)-4-[{3-[2-(dimethylamino)ethyl]-1H-indol-5-yl}methyl]-2-oxazolidinone (zolmitriptan), which belongs to the group of triptans used for the treatment of migraine.

BACKGROUND ART

Synthesis of zolmitriptan consists of three generally known reactions (WO97/06162): diazotation of (S)-4-(4-aminobenzyl)-1,3-oxazolidin-2-one of formula I with a nitrite in the environment of diluted hydrochloric acid, subsequent reduction of the resulting diazonium salt to the hydrochloride of (S)-4-(4-hydrazinobenzyl)-1,3-oxazolidin-2-one of formula IV and finally its condensation with 4,4-diethoxy-N,N-dimethylbutylamine of formula II, which, in an acidic environment, according to Fischer, provides an indole skeleton—in this case zolmitriptan of formula III—in a mechanism analogous to the benzidine rearrangement. The whole synthesis occurs in an aqueous environment and does not require isolation of intermediates.

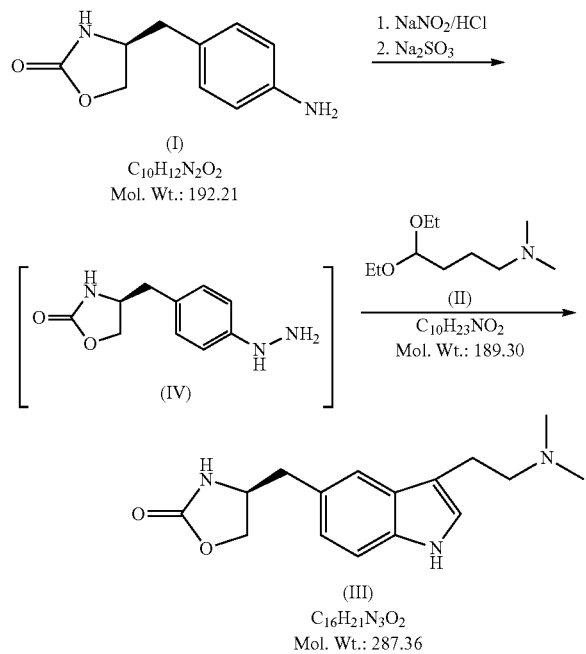

As the reduction reagent in the reduction stage of the synthesis stannous chloride or an alkali sulphite, e.g. $Na_2SO_3$ (WO97/06162), is used. However, the use of stannous chloride causes problems with purification of the product and wastewater from environmentally undesirable tin salts and this is why it is not suitable in the production scale. On the other hand, $Na_2SO_3$ is relatively poorly soluble, which results either in the need of stronger dilution of the reduction mixture or in a heterogeneous reaction system (suspension). Heterogeneous reactions may then cause problems with stirring, especially in a larger scale, while dilution of the reaction mixture requires a substantial extension of the reaction time. The second stage of the reduction carried out in an acidic environment at 60° C. in this homogeneous diluted solution usually takes up to 18 hours (WO 97/06162), which, besides energy and personnel costs, also increases the undesirable heat load of the intermediate product and reduces the yield of the synthesis.

The raw product is usually recovered from the reaction mixture after its alkalization (NaOH/water) by repeated extraction with an organic solvent, generally ethyl acetate (WO 97/06162). After concentration of the extracts to a fraction of the initial volume crystalline raw zolmitriptan is obtained in the form of a solvate with ethyl acetate, which is purified through re-crystallization from the ethanol-ethyl acetate mixture and subsequently desolvated by stirring in aqueous acetone. The product—zolmitriptan base—is finally removed by filtration and washed with ethyl acetate.

However, with regard to relatively low solubility of zolmitriptan in ethyl acetate the above mentioned extraction method of isolation requires considerable volumes of the extraction agent (approx. 25-fold of the final product) and their subsequent evaporation. To say nothing of the energy and time demands of such a method, during concentration in a larger scale the product is also subject to considerable heat load which is, with regard to the increased temperature and character of the solvent, even multiplied by the mutual reactivity of the product (basic amine) with the solvent (ester) and also by hydrolysis of the product and solvent caused by the alkaline aqueous environment during the extractions.

For this reason conditions that would be able to eliminate or minimize the above mentioned negative aspects of the hitherto known methods of zolmitriptan synthesis have been sought.

DISCLOSURE OF INVENTION

The invention consists in an improved method of manufacturing (S)-4-[{3-[2-(dimethylamino)ethyl]-1H-indol-5-yl}methyl]-2-oxazolidinone (zolmitriptan), which is based, on one hand, on optimization of the reaction conditions in the reduction stage when a salt, e.g. chloride, of (S)-4-(4-benzyldiazonium)-1,3-oxazolidin-2-one is reduced in an aqueous solution to (S)-4-(4-hydrazinobenzyl)-1,3-oxazolidin-2-one by the effect of an alkali metal disulphite, and, on the other hand, on a new method of isolation of the final product (zolmitriptan of formula III), which consists in isolation of the raw toluene solvate of zolmitriptan as an intermediate product, its purification and desolvatation.

Another aspect of the invention includes preparation of the hitherto not described solvate of zolmitriptan with toluene, which can be preferably used for the isolation of raw zolmitriptan from the reaction mixture and its further purification.

DESCRIPTION OF INVENTION

It has been found out experimentally that an alkali metal disulphite, most preferably $Na_2S_2O_5$, is a suitable reduction agent for reduction of the diazonium salt to (S)-4-(4-hydrazinobenzyl)-1,3-oxazolidin-2-one since it is substantially more soluble in water and at the same time cheaper than $Na_2SO_3$. It is suitable at the same time to adjust the pH of the solution of the reduction agent with a smaller quantity of an alkali metal hydroxide (e.g., NaOH)—¼ to ½ of the used $Na_2S_2O_5$ on the molar basis. The amount of water required for formation of a stable homogeneous solution at temperatures around 0° C. is only 2.5-3-fold of the used $Na_2S_2O_5$ and the time required for the acidic stage of the reaction at 60° C. and pH≈0 (HCl) is only 5-6 hours, i.e. only a third of the time required at normal higher dilution. In addition, the composition of samples drawn from the mixture during the reaction measured by means of HPLC and LC-MS shows that with the use of a disulphite the reaction mechanism of the reduction is different from that expected in the case of reduction with a sulphite.

Before the final Fischer synthesis the reaction mixture is diluted with water (approx. half the volume with regard to the reaction mixture), 4,4-diethoxy-N,N-dimethylbutylamine of formula II is added and the mixture is refluxed at pH=0.6-1 and temperature of approx. 98° C. for 2.5 hours. This means that the whole reaction sequence can be carried out in three-shift operation within a single day.

Another aspect of the invention includes a completely new method of isolation of zolmitriptan in the form of the hitherto not described toluene solvate. It is based on the observation that from the aqueous reaction mixture after the Fischer reaction, to which a small quantity of toluene is added and emulsified, solid zolmitriptan crystallizes during slow alkalization with an aqueous solution of an alkali metal carbonate or hydroxide, e.g. NaOH or $K_2CO_3$. The crystalline raw product obtained this way contains 9-14% by weight of toluene according to gas chromatography. This result is in compliance with the record obtained by thermogravimetric analysis (FIG. 1), which documents a quick loss of approx. 10% of mass around 111° C. corresponding to the boiling point of toluene at normal pressure. The established content of toluene thus corresponds to the probable molar representation of toluene in the crystal lattice of 1:2 (13.8% by weight).

The new crystalline form of zolmitriptan with toluene incorporated in its crystal lattice is clearly characterized by strong Raman bands at 1354 and 1443 $cm^{-1}$ together with characteristic bands of toluene (at 786 and 1014 $cm^{-1}$) in the Raman spectrum of the solvate (FIG. 2). For clearness, the Raman spectrum of raw zolmitriptane solvate (black dashed line) is compared here with the spectra of pure zolmitriptan (full black) and free toluene (full grey).

The raw toluene solvate of zolmitriptan can be purified by re-crystallization from common solvents, e.g. alcohols, acetone, ethyl acetate and the like, or their mixtures or mixtures with toluene. Re-crystallization from solvents not containing toluene can also be used for desolvatation of the product. Desolvatation can also be achieved with the use of long-term drying under reduced pressure at temperatures of 60 to 100° C.

Desolvatation and at the same time re-purification of the raw product can be advantageously achieved by dissolution of the zolmitriptan solvate in a diluted aqueous solution of an acid, e.g. HCl, and subsequent separation of the immiscible organic phase (toluene). The remaining aqueous solution of the zolmitriptan salt is then converted to the free base by gradual addition of an alkali metal carbonate or hydroxide, e.g., $K_2CO_3$ or NaOH, etc., in the solid state or in solution. The water-insoluble base is then filtered off and washed with aqueous alcohol and water.

The free zolmitriptane base (form A) can be purified by re-crystallization from an ethanol-water mixture. The resulting white or almost white product (HPLC ~100.0%) corresponds, according to the X-ray analysis, to form A, the same one as can be prepared by the method in accordance with patent application no. WO 97/06162.

Advantages of the above mentioned isolation and purification process include the speed, low price of input materials, a high yield and quality of the obtained product and mainly minimum impacts on the environment since except small volumes of toluene and ethanol no organic solvents are used in the whole process. The method of isolation of raw zolmitriptan from the reaction mixture in accordance with the invention makes it possible to completely remove all the above mentioned problems that in the production scale accompany the hitherto used method of isolation based on extraction with ethyl acetate.

EXAMPLES

Example 1

Diazotation of (S)-4-(4-aminobenzyl)-1,3-oxazolidin-2-one of formula (I)

Figure 1:
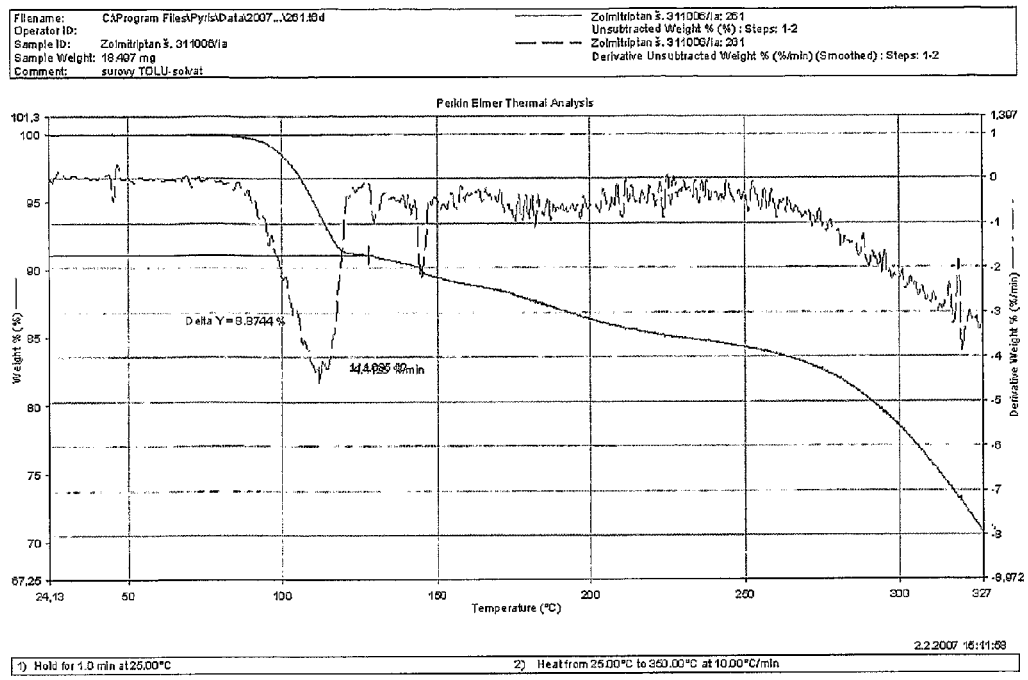
FIG. 1 shows a record of thermogravimetric analysis (TGA) of the raw toluene solvate of zolmitriptan prepared in accordance with Example 4—temperature dependence of the sample weight loss in % showing the maximum loss around 111° C. (full line) and the corresponding first derivation (dashed).
Figure 2:
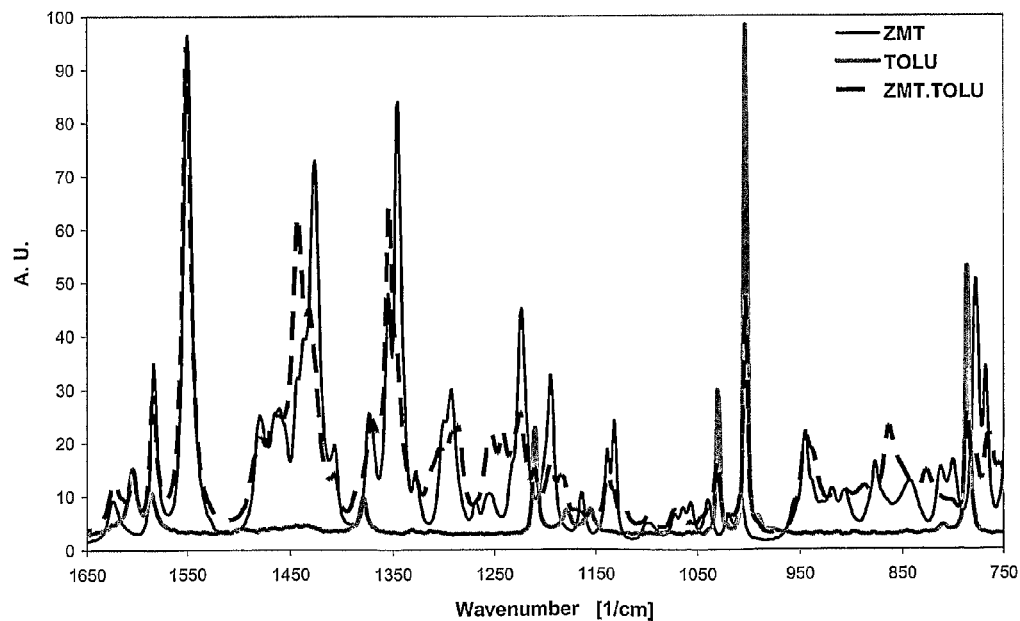
FIG. 2 shows the Raman spectrum of the raw toluene solvate of zolmitriptan prepared in accordance with Example 4 (dashed black line) compared to the spectrum of pure unsolvated zolmitriptan (full black) and free toluene (full grey).

2.4 liters of concentrated HCl are added to 7.0 liters of water in a duplicator. In such diluted HCl 1.75 kg of (S)-4-(4-aminobenzyl)-1,3-oxazolidine-2-one of formula (I) is stirred up and the mixture is cooled down to 0° C. under stirring. During the cooling an aqueous solution of $NaNO_2$ (0.64 kg $NaNO_2$/1.4 liters of water) is prepared for diazotation. At the temperature of ca. 0° C. a solution of $NaNO_2/H_2O$ is slowly added to the solution of the starting substance (I) on intensive stirring and cooling. After adding of all the nitrite the mixture is further stirred at ca. 0° C. for ca. 30 min.

Example 2

Reduction of the Diazonium Salt

Weighed 0.28 kg of NaOH is dissolved in 7.0 liters of water and of 2.66 kg of sodium disulphite are added under stirring. After dissolution the mixture is cooled to ca. 2° C. The diazonium salt solution is slowly added to the cooled disulphite solution under intensive stirring at the temperature of 2-5° C. The mixture is then stirred at ca. 5° C. for additional 30 minutes. Then, it is heated up to ca. 25° C. and stirred at this temperature for 45 minutes. Further it is heated under a reflux condenser to ca. 60° C. while being stirred. After heating 900 ml of concentrated HCl is added to the reaction mixture and the mixture is stirred under the reflux condenser for another 5 hours. Then the mixture is diluted with 14 liters of water.

Example 3

Fischer Indole Reaction

The diluted reaction mixture is heated up to ca. 90° C. 1.75 kg of 4,4-diethoxy-N,N-dimethylbutylamine of formula II is weighed. The weighed acetal (II) is added to the reaction mixture, which is then brought to moderate reflux (at ca. 98° C.) and being stirred under the reflux condenser it is left to react for about 2.5 hours. After 2.5 hours from the start of the reflux the heating of the mixture is switched off and the reaction mixture is cooled to the laboratory temperature.

Example 4

Isolation of the Raw Toluene Solvate of ZOLMITRIPTAN

At the laboratory temperature and being stirred the cooled mixture is neutralized with a ca. 20% aqueous solution of NaOH. About 4 liters of toluene is added and the mixture is stirred to make an emulsion. Then, an aqueous solution of NaOH is slowly added under stirring until pH of ca. 9.5 is achieved. After approx. 30 minutes of stirring the solid product is filtered off and washed with water. It is dried at temperatures of about 30° C. to the constant weight (about 10 hours).

Example 5

Desolvatation and Purification of the Toluene Solvate of ZOLMITRIPTAN by Conversion into a Salt Being stirred at the laboratory temperature the toluene solvate of zolmitriptan is dissolved in 12 liters of 2% aqueous solution of HCl. After the dissolution of the solid phase the mixture is left to separate for ca. 15 minutes—toluene creates the upper layer. The lower aqueous solution of the salt of the product is separated and mixed with about 2.5 liters of ethanol. The mixture is further stirred and at the temperature of about 25° C. a total of 1.0 kg of potassium carbonate is added in several approximately equal doses. About 30 min after the last addition the suspension of the product is cooled to ca. 15° C. while being stirred and approx. after 1 hour of stirring the base is filtered off. The filtration cake is washed with ca. 2 liters of purified water and left to dry under normal pressure at the temperature of ca. 45° C. to the constant weight.

The invention claimed is:

1. A method for the preparation of (S)-4-[{3-[2-(dimethylamino)ethyl]-1H-indol-5-yl}methyl]-2-oxazolidinone (zolmitriptan) of formula III

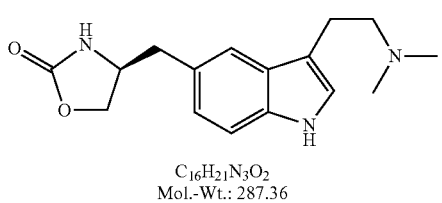

$C_{16}H_{21}N_3O_2$
Mol.-Wt.: 287.36 comprising the following scheme

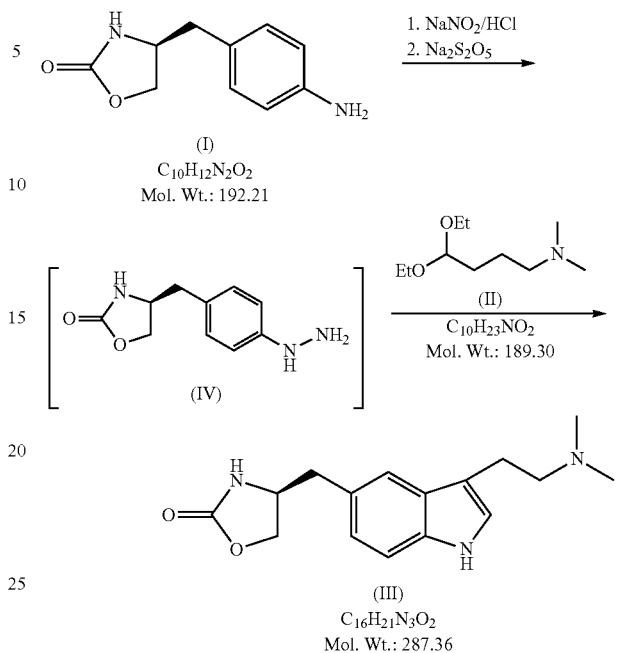

wherein the reduction of the diazonium salt to (S)-4-(4-hydrazinobenzyl)-1,3-oxazolidin-2-on of formula IV is carried out in the presence of an alkali metal disulphite.

2. The method in accordance with claim 1, wherein the product of formula III is first isolated in a form of a toluene solvate, which is further transformed to the unsolvated form.

3. The method in accordance with claim 2, wherein after the reaction is complete, toluene and an alkali metal carbonate or hydroxide, or their aqueous solution, are added to the reaction mixture.

4. The method in accordance with claim 2, wherein the toluene solvate is transformed to the unsolvated substance by drying at a temperature between 60 to 100° C.

5. The method in accordance with claim 2, further comprising the steps of desolvation and purification of the toluene solvate of zolmitriptan, to form the zolmitriptan base, wherein the toluene solvate is dissolved in a diluted acid, the upper inmiscible toluene phase is separated from the mixture and zolmitriptan is then released from the remaining acidic aqueous solution by addition of an alkali metal carbonate or hydroxide or their aqueous or alcoholic solutions.

6. The method according to claim 1, wherein the alkali metal disulphite is sodium disulphite.

7. The method according to claim 3, wherein the alkali metal carbonate or hydroxide is potassium carbonate ($K_2CO_3$) or sodium hydroxide (NaOH).

8. The method according to claim 5, wherein the diluted acid is hydrochloric acid (HCl).

* * * * *